(12) United States Patent
Flaherty et al.

(10) Patent No.: US 6,685,716 B1
(45) Date of Patent: Feb. 3, 2004

(54) OVER-THE-WIRE APPARATUS AND METHOD FOR OPEN SURGERY MAKING OF FLUID CONNECTION BETWEEN TWO NEIGHBORING VESSELS

(75) Inventors: J. Christopher Flaherty, Los Altos, CA (US); Philip C. Evard, Palo Alto, CA (US)

(73) Assignee: Transvascular, Inc., Menlo Park, CA (US)

( * ) Notice: Subject to any disclaimer, the term of this patent is extended or adjusted under 35 U.S.C. 154(b) by 0 days.

(21) Appl. No.: 09/478,109

(22) Filed: Jan. 4, 2000

(51) Int. Cl.$^7$ .............................................. A61B 17/32
(52) U.S. Cl. ..................................................... 606/159
(58) Field of Search ........................... 606/52, 53, 153, 606/154, 159, 184, 185, 174, 205, 207, 170, 151, 156–158, 209

(56) References Cited

U.S. PATENT DOCUMENTS

| | | | | |
|---|---|---|---|---|
| 2,025,345 A | * | 12/1935 | Harris | 30/131 |
| 3,503,398 A | * | 3/1970 | Fogarty et al. | 606/207 |
| 3,807,406 A | * | 4/1974 | Rafferty et al. | 30/133 |
| 4,236,470 A | * | 12/1980 | Stenson | 112/169 |
| 4,300,564 A | * | 11/1981 | Furihata | 600/103 |
| 4,345,600 A | * | 8/1982 | Rothfuss | 606/148 |
| 4,373,530 A | * | 2/1983 | Kilejian | 606/145 |
| 4,947,852 A | | 8/1990 | Nassi et al. | |
| 5,014,433 A | * | 5/1991 | Tepic | 30/248 |
| 5,246,007 A | | 9/1993 | Frisbie et al. | |
| 5,279,565 A | * | 1/1994 | Klein et al. | 604/105 |
| 5,391,174 A | * | 2/1995 | Weston | 606/148 |
| 5,439,478 A | * | 8/1995 | Palmer | 600/564 |
| 5,471,992 A | * | 12/1995 | Banik et al. | 600/564 |
| 5,490,856 A | * | 2/1996 | Person et al. | 227/175.1 |
| 5,556,404 A | * | 9/1996 | Belanger et al. | 425/427 |
| 5,667,473 A | * | 9/1997 | Finn et al. | 385/117 |
| 5,667,478 A | * | 9/1997 | McFarlin et al. | 385/117 |
| 5,715,827 A | | 2/1998 | Corl et al. | |
| 5,716,320 A | * | 2/1998 | Buttermore | 600/104 |
| 5,830,224 A | | 11/1998 | Cohn et al. | |
| 5,857,961 A | * | 1/1999 | Vanden Hoek et al. | 600/104 |
| 5,931,810 A | * | 8/1999 | Grabek | 604/115 |
| 6,086,528 A | * | 7/2000 | Adair | 600/104 |
| 6,139,508 A | * | 10/2000 | Simpson et al. | 600/564 |
| 6,206,904 B1 | * | 3/2001 | Ouchi | 600/104 |
| 6,217,549 B1 | * | 4/2001 | Selmon et al. | 604/104 |
| 6,358,268 B1 | * | 3/2002 | Hunt et al. | 606/206 |
| 6,368,327 B2 | * | 4/2002 | Lippitt et al. | 606/110 |

* cited by examiner

Primary Examiner—Michael J. Milano
Assistant Examiner—D. Jacob Davis
(74) Attorney, Agent, or Firm—Cohen & Sakaguchi LLP; William A. English (57) ABSTRACT

The invention provides a wire guided aperture creating apparatus, an over-the-wire kit, and a method for creating a hole in adjacent portions of first and second anatomical conduits during a surgical procedure. The apparatus includes an elongated element having a guidewire lumen and an aperture creating assembly disposed near the distal end of the elongated element. In a further embodiment the device may include first and second elongated elements coupled via a coupler and an aperture creating assembly disposed between the elements. At least one of the elements includes a passage-defining element permitting passage therethrough of a first guidewire. In addition to the devices identified above, the kit includes a first guidewire for insertion into a lumen of the first vessel to an initial cutpoint and then through adjacent portions of sidewalls of the first and second vessels into a lumen of the second vessel. The method involves inserting a first guidewire into a lumen of a first vessel to an initial cutpoint and then though adjacent portions of sidewalls of the first vessel and a second vessel into a lumen of the second vessel. The method further involves providing a wire guided aperture creating apparatus as identified above, and inserting the device over the first guidewire such that the passage-defining element passes over the first guidewire.

32 Claims, 5 Drawing Sheets

OVER-THE-WIRE APPARATUS AND METHOD FOR OPEN SURGERY MAKING OF FLUID CONNECTION BETWEEN TWO NEIGHBORING VESSELS

FIELD OF THE INVENTION

The present invention relates to devices and methods for accessing adjacent anatomical conduits with an aperture creating assembly that can be operated over a guidewire that has been initially placed between the conduits to maintain access to the connection site. The present invention further relates to the field of treatment of diseased, injured or occluded vessels or other anatomical or synthetic structures, having restricted, blocked or insufficient fluid flow, and in particular, to providing a fluid connection between neighboring vessels or other adjacently situated anatomical or synthetic structures having hollow lumens or cavities formed therein.

BACKGROUND OF THE INVENTION

Restricted or blocked fluid flow in vessels or other anatomical structures, such as, for example, restricted or blocked arterial flow in coronary arteries, or other blood vessels, can result in pain, dysfunction and even death. Other vessels or structures which may experience restricted or blocked flow include blood vessels, vas deferens, fallopian tubes, intestines, lymphatic ducts, grafts, and chambers of the heart or brain.

Certain percutaneous revascularization bypass procedures have been devised wherein blood flow passageways (e.g., puncture tracts or interstitial tunnels) are formed between the lumens of adjacently situated blood vessels (e.g., between an obstructed coronary artery and an adjacent coronary vein) to bypass a diseased, injured or obstructed segment of one blood vessel. These procedures have previously been described in, for example, U.S. Pat. No. 5,830,222, assigned to the assignee of the present invention and incorporated by reference herein. Also, Provisional U.S. Patent Application Serial No. 60/010,614, also assigned to the assignee of the present invention, and incorporated herein by reference, particularly describes certain percutaneous revascularization grafting procedures devised for by-passing an obstructed artery. In these grafting procedures, a tubular graft (e.g., a segment of an endogenous blood vessel or a tube graft formed of natural or synthetic material) is adjacent or maneuvered to be adjacent to the obstructed artery. With procedures originating within the vasculature, one or more openings are formed in the graft and the adjacent artery. The openings formed in the graft are then connected to the openings formed in the artery, such that blood may flow between the graft and the artery. In these techniques, all operations are performed from within a blood vessel and generally from a remote location. For example, access to the vascular system may be gained in the groin. Long catheters are introduced from the vascular access so that a distal end of the catheter is passed through the vasculature to the by-pass site. The various cutting and vessel-to-vessel junctions are established at the by-pass site using controls operated by the surgeon at the proximal end of the catheter (i.e. at the point of access to the vascular system). In some situations, however, such percutaneous procedures are difficult, if not impossible to perform, the patient may be involved in a simultaneous surgical procedure or the clinician may prefer a surgical approach and it is desirable to effect by-passes with an open surgical procedure.

It is an object of the invention to provide new kits, devices and methods for the simplified formation of fluid passageways between adjacent portions of anatomical structures, such as blood vessels, during an open surgical procedure so that fluid flow may be provided in areas where vessels have been restricted or blocked inhibiting or eliminating fluid flow therein.

SUMMARY OF THE INVENTION

The invention is directed against the partial or complete blockages of fluid flow between anatomical structures. The invention provides over-the-wire kits, devices and methods useful in an open surgical field, for forming apertures in adjacent portions of anatomical structures such as blood vessels during a surgical procedure. The invention's kits, devices and methods may be useful for creating alternative vascular channels to provide revascularization routes in the heart between the coronary arteries and between the cardiac veins, or in the periphery between adjacent veins, conduits and/or arteries. The kits, devices and methods of the invention may also be used to by-pass coronary arteries and to provide for cardiac venous arterialization. It will be understood by persons of ordinary skill in the art, however, that the general kits, devices and methods as described herein are equally applicable to the surgical manipulation of any anatomical structure for providing the passage of fluid flow therebetween. As used herein, the term "anatomical structures" or "blood vessels" includes blood vessels, tubes, ducts, hollow organs, brain or heart chambers, grafts and synthetic structures.

In one aspect, the invention provides an over-the-wire kit for forming apertures in adjacent portions of a first blood vessel and a second blood vessel during a surgical procedure. The kit includes at least a first guidewire for introduction into a lumen of the first vessel to an initial cutpoint, and then through adjacent portions of sidewalls of the first vessel and the second vessel into a lumen of the second vessel. As used herein, the phrase "initial cutpoint" refers to a position on the sidewall of the first vessel at which it is desired to establish a passage therethrough leading to the second vessel. The guidewire is preferably introduced in an open surgical field, such as pursuant to a conventional open chest procedure. The point at which the wire is introduced into the lumen of the first vessel may be near (or opposite) the initial cutpoint. Alternatively, that point of introduction may be a distance along the vessel from the initial cutpoint.

The kit also includes a wire guided aperture creating apparatus. The aperture creating apparatus is adapted to "follow" the wire, typically passing initially through a sidewall of a first vessel, through the lumen of that vessel to the initial cutpoint in the sidewall of the first vessel and then through the sidewalls of the first and second vessels, establishing apertures in those sidewalls. In one form, the aperture creating apparatus includes a first elongated element extending along a first axis between a proximal end and a distal end. That aperture creating apparatus also includes a second elongated element extending along a second axis between a proximal end and a distal end. The first elongated element is coupled to the second elongated element whereby the first axis substantially intersects the second axis at a common intersection point spaced apart from the distal ends of the elongated elements. The distal end of the first elongated element is movable with respect to the distal end of the second elongated element about an axis orthogonal to the first axis and the second axis. A tissue cutting assembly is disposed between the first and second elongated elements. At least one of the first and second elongated elements includes a passage-defining element permitting passage therethrough of the first guidewire. In an alternate form, the kit includes a second guidewire, and the second elongated element also includes a passage-defining element, permitting passage therethrough of the second guidewire.

In one form, the cutting assembly is scissors-like, with the first and second elongated elements being rigid, and being pivotally joined at a common intermediate point, to form pivoting, opposed scissors-like blades on one side of the intermediate point and to form handles on the other side. At least one of the blades includes a channel for the first guidewire to pass through. The edges of the opposed elongated elements provide the tissue cutting assembly, as in a conventional scissors.

In another form of the invention, the wire guided aperture creating apparatus may be formed from a flexible catheter with a bifurcated distal end, forming two opposed jaw-like elongated elements which are moveable in opposite directions about an axis transverse to the catheter at the point of bifurcation. The elongated elements may be flexible or rigid at least near their distal ends. In this form, the one (or both, in two-wire configurations) elongated elements has a passage extending therethrough for passing over a guidewire. A tissue cutting assembly is disposed between the elongated elements.

In various forms of the invention, and by way of example, the tissue cutting assembly may include a blade positioned at the point of intersection or bifurcation, pointing away therefrom. Alternatively, one of the elongated elements may house a longitudinally extending blade and the other element may house an anvil, which when the elongated elements are moved toward each other, can effect cutting of tissue therebetween. Alternatively, a laser cutter, or radio frequency (rf) cutter or hole punch (with anvil) may be positioned between the opposing elongated elements.

In the method of the invention, a one (or two) wire kit of the above described form is used. Initially, in an open surgical field, a lead end of first guidewire is passed through a veinotomy in a vein (the first blood vessel) and into its lumen. The lead end of the first guidewire is then advanced through the lumen until reaching a desired point (referred to as the initial cutpoint) of a junction between the first blood vessel and an adjacent artery (the second blood vessel). The lead end is then passed through the adjacent sidewalls of the first and second vessels and into the lumen of the second vessel. In a two wire procedure, a second guidewire is passed through the veinotomy and into the lumen of the first blood vessel and as advanced so that its lead end is disposed within that lumen but extends beyond the initial cutpoint.

Following insertion of the guidewire(s), the path defining element of the first elongated element of the guided wire aperture creating apparatus is passed over the first guidewire, and the distal ends of the elongated elements are fed through the veinotomy into the lumen of the first blood vessel. The wire guided aperture creating apparatus is advanced in that lumen, with the first elongated element tracking the first guidewire. Upon reaching the initial cutpoint, the first elongated element is led (by the first guidewire) from the lumen of the first blood vessel to the lumen of the second blood vessel, with the second elongated elements remaining in the lumen of the first blood vessel. In two wire procedures, the second elongated element is fed over the second guidewire at the same time that the first elongated element is fed over the first guidewire. Then, as the wire guided aperture creating apparatus is advanced just beyond the initial cutpoint, the first elongated element follows the first guidewire to the lumen of the second blood vessel, and the second elongated element affirmatively follows the second guidewire to continue in the lumen of the first blood vessel.

With the wire guided aperture creating apparatus so positioned just beyond the initial cutpoint, the tissue cutting assembly is then operated to cut tissue between the first and second elongated elements (i.e., simultaneously, the walls of the first and second blood vessels). In the scissors-like forms of the invention, handles can be operated to drive the blades to cut the tissue. In the other forms, the various aperture creating assemblies are operative to cut the tissue between the first and second elongated elements. For example, where there is an outwardly facing blade at the intersection or bifurcation point, the wire guided aperture creating apparatus need only be advanced so that the blade effects the cutting. For example, a laser or rf source near the distal end of one of the elongated elements might be actuated to ablate tissue between the elongated elements. Alternatively, the elongated elements may be driven toward each other so that a blade or punch on one elongated element cuts tissue between it and an anvil on the other elongated element. Following the effecting of a desired length cut, the wire guided aperture creating apparatus is withdrawn from the blood vessels and the adjacent vessels may be further joined, if necessary. A scaffolding device, or other treatment may be provided to the aperture site for the purpose of maintaining fluid flow.

In another form of the invention, the aperture creating apparatus is adapted to follow the guidewire, following introduction of that wire into the lumen of the first vessel and positioning that wire to the initial cutpoint and through the sidewalls of the first and second vessels and into the lumen of the second vessel. As the lead end of the aperture creating apparatus follows (i.e., is guided by) the wire and passes through the sidewalls of the first and second vessels, a tissue cutting, tissue removing, tissue ablating or tissue enlarging assembly cuts, removes, ablates or enlarges, the portions of those sidewalls adjacent to the guidewire, establishing a passageway connecting the lumens of the first and second vessels.

The aperture creating apparatus in this form is a rigid or flexible catheter-like structure that is fed over the guidewire, having a tissue cutting, tissue removing, tissue ablating or tissue enlarging element at its lead end. In various forms of the invention, the tissue cutting, tissue removing, tissue ablating or tissue enlarging element can vary. For example, that element may include a remote actuated inflatable balloon (concentric or eccentric with respect to the axis of the catheter) at or near its distal tip, or may include a remotely retractable or fixed cutting blade (or blades) at or near the catheter distal tip, or may include a remote actuated rf ablation electrode (concentric or eccentric) at or near the catheter distal tip, or may include a laser at or near the catheter tip. An orientation marker may be included on devices having eccentric placement of the aperture creating assembly relative to the body of the elongated element. The elongated element may include a implantable scaffolding device which can be used to create the aperture and can be left permanently implanted to scaffold the aperture sites. Furthermore, a hemostasis apparatus may be included the passage defining element, or guidewire lumen, to prevent leakage of blood through the lumen.

The invention also is a kit including a guidewire and the latter-described aperture creating apparatus.

BRIEF DESCRIPTION OF THE DRAWINGS

For a fuller understanding of the nature and the objects of the invention, reference should be made to the following detailed description and the accompanying drawings in which like reference numerals refer to like elements and in which.

DETAILED DESCRIPTION OF THE PREFERRED EMBODIMENTS

Figures 1A, 1B, 2A, 2B, 2C, 2D, 2E:
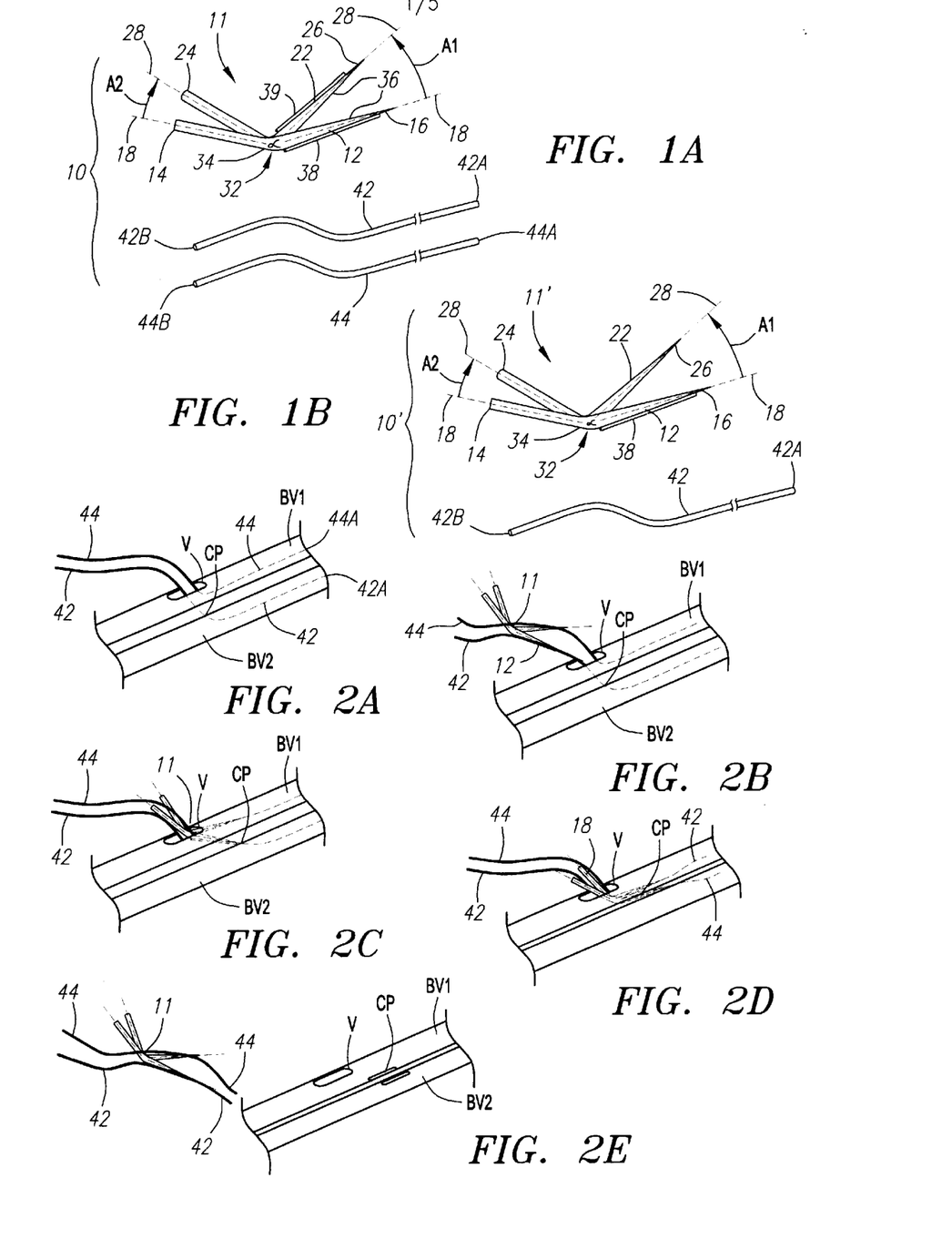
FIG. 1A is a schematic representation of an over-the wire kit according to the invention adapted for "two wire" procedure.
FIG. 1B is a schematic representation of an alternate form of the over-the-wire kit of the invention adapted for "one wire" procedure.
FIGS. 2A–2E illustrates the method of the invention.

Exemplary over-the-wire kits 10 of the invention are illustrated in FIGS. 1A and 1B. As illustrated in FIG. 1A, the "two wire" kit 10 includes a wire guided aperture creating apparatus 11 and first guidewire 42 and a second guidewire 44.

The illustrated aperture creating apparatus 11 has the general form of a scissors including a first elongated element 12 extending between a proximal end 14 and a distal end 16. The first elongated element 12 extends along a first axis 18.

The wire guided aperture creating apparatus 11 also includes a second elongated element 22 extending between a proximal end 24 and a distal end 26. The second elongated element 22 extends along a second axis 28. The first element 12 is coupled to the second element 22 at a coupler 32. The first axis 18 substantially intersects the second axis 28 at an intersection point 34. The distal end 16 of the first element 12 is movable with respect to the distal end 26 of the second element 22 about an axis orthogonal to the first axis 18 and the second axis 22 at the intersection point 34. As described below, a tissue cutting assembly 36 is disposed between the first element 12 and the second element 22 elements. In the embodiment of FIG. 1A, the elongated elements 12 and 22 are rigid and scissors-like having blades extending from point 34 to the distal ends 16, 26 and handles extending from point 34 to proximal ends 18, 28. The blades are dimensioned to fit in the blood vessels of interest, and form the cutting assembly as conventional style scissors blades.

As illustrated, the axes 18 and 28 near the distal ends 16 and 26, form an angle A1 about a axis which is orthogonal to axes 18 and 28 at point 34. Those axes 18 and 28 near the proximal ends 14 and 24 form an angle A2 about the orthogonal axis at point 34. In that embodiment the handles are angularly offset from the blades (i.e. the bisector of angle A1 is angularly offset from the bisector of angle A2, for each of use of apparatus 11.

In the illustrated embodiment, each of the first element 12 and the second 22 elements includes an associated one of passage-defining elements 38 and 39, extending between points 34 and its distal end permitting passage therethrough of one of wires 42 and 44.

While in FIG. 1A, the passage defining elements 38 and 39 shown as discrete cylindrical tubes affixed to an associated one of elongated elements 12 and 22; the elements 38 and 39 may have other forms, for example, channels passing through the interior of elements 12 and 22, or as pairs of ring-like guides at opposite ends of the blades of each of elements 12 and 22.

The guidewire 42 extends between a distal (or lead) end 42A and a proximal end 42B. Similarly, the guidewire 44 extends between a distal (or lead) end 44A and a proximal end 44B.

FIG. 1B shows "one wire" kit 10' similar to the kit 10 of FIG. 1A, but is adapted for "one-wire" procedures. In FIG. 1B, there are no equivalents to the wire 44 and passage defining elements 39.

The use of the kit 10 is shown in FIGS. 2A–2E for establishing holes in adjacent sidewalls of two blood vessels BV1 (vein) and BV2 (artery) at an initial cutpoint CP. Initially, in an open surgical field, a veinotomy V is made in blood vessel BV1 near the initial cutpoint CP. Then as shown in FIG. 2A, guidewire 42 is introduced through veinotomy V and its lead end 42A is advanced toward initial cutpoint CP. When at point CP, the lead end 42A is first driven through the sidewall of BV1 and then the sidewall of BV2 into the lumen of BV2. By way of example, the vessel-to-vessel passage of lead end 42A may be effected using a guidewire having a flexible tip and in addition possibly a preformed J-shaped end 42A which is inserted within close-fitting tubular sheath or needle (so that the preformed J-shape is distorted to match the inner lumen of the sheath) until the sheath passes through the initial cutpoint and reaches the lumen of the BV2. At that point, the sheath is maintained relatively stationary and wire 42 is advanced so that, while the guidewire 42 is advanced, the lead end 42A emerges from the sheath. Lead end 42 then reverts to its J-shape, if in place, and advances down the lumen of BV2. Following, or prior to, that placement of lead end 42A of wire 42, the lead end 44A of wire 44 is introduced into veinotomy V and advanced within BV1 to a point beyond the initial cutpoint CP, as shown in FIG. 2A.

As shown in FIG. 2B, the wire guided apparatus 11 is then positioned over wires 42 and 44 so that wires 42 and 44 are within path-defining elements 38 and 39, respectively.

Then, as shown in FIG. 2C, the distal ends of apparatus 11 are introduced into veinotomy V. The apparatus 11 is advanced to initial cutpoint CP, where the elongated element 12 tracks wire 42 into BV2, while elongated element 22 tracks wire 44 and remains in BV1, as shown in FIG. 2D. Then the surgeon drives the handles of apparatus 11 so that the blades close simultaneously cutting the portions of the sidewalls of BV1 and BV2 between the blades. Following that cut operation, the cutting apparatus 11 and wires 42 and 44 are withdrawn from BV1 and BV2 as shown in FIG. 2E. Then a bridging connection can be established between BV1 and BV2, for example, using the couplers shown in the incorporated reference U.S. Pat. No. 5,830,222.

In a "one-wire" procedure, the kit of FIG. 1B may be used in a similar manner to the method described above, but where the elongated element 22 merely remains in BV1 without tracking a guidewire.

Figure 3:
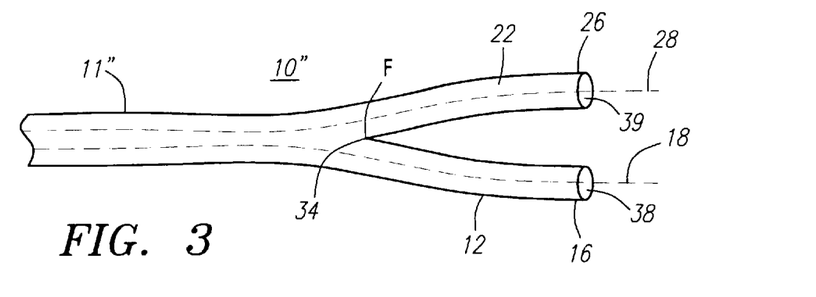
FIG. 3 is a schematic representation of an alternative wire guided aperture creating apparatus of the over-the-wire kit of the invention.
Figure 4A:
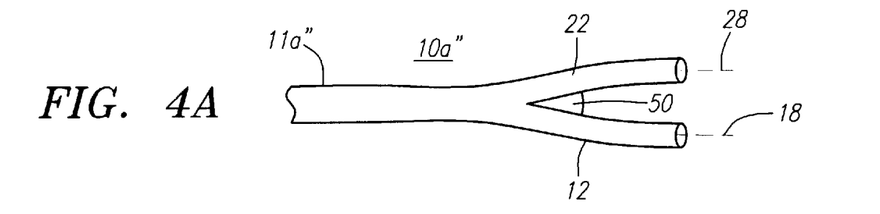
FIGS. 4A–4E illustrate variants of the wire guided aperture creating apparatus of the invention.
Figure 4B:
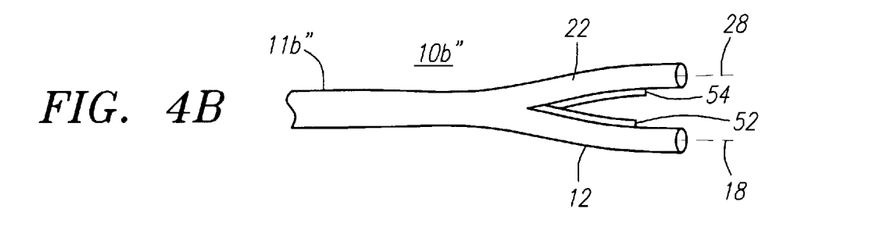
Figure 4C:
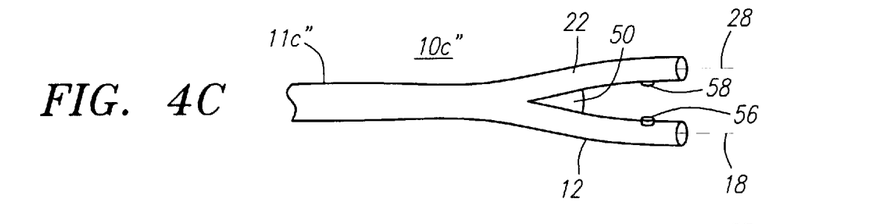
Figure 4D:
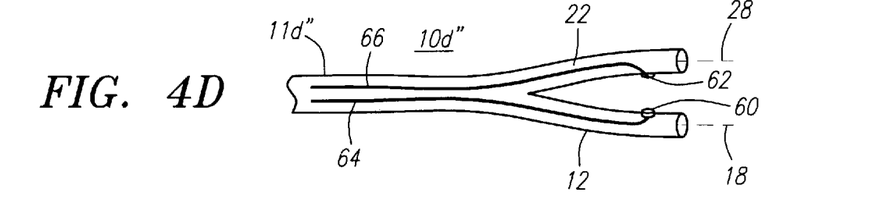
Figure 4E:
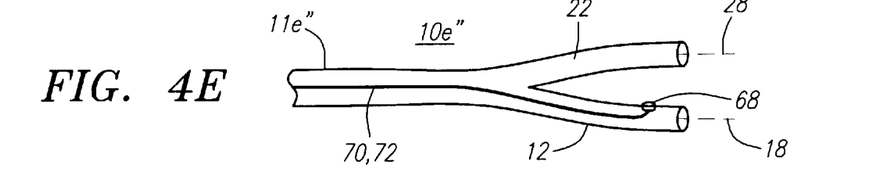

While the wire-guided aperture-creating apparatus described above is a rigid scissors-like form, a wire guided aperture creating apparatus of the invention may have alternate forms. An alternate embodiment is shown in FIG. 3. In FIG. 3, the aperture-creating apparatus 10" is in the form of a flexible catheter 11" having a bifurcation at its distal end defining elongated elements 12 and 22 having distal ends 16 and 26 respectively, and extending along axes 26 and 28 respectively. The catheter 11" has a flexure F at the junction 34 of the bifurcated portions so that the distal ends 616, 626 are moveable with respect to each other about an axis orthogonal to axes 18 and 28 at point 34. As illustrated in FIG. 3, each of the distal ends 16 and 26 includes a respective one of passage-defining aperture 38, 39, each being suitable for tracking over a respective one of guidewires 42 and 44. In "one-wire" kits, the aperture 39 may not be present. In various forms of the embodiment of FIG. 3, the bifurcated ends may be flexible, or relatively stiff or rigid. In the forms of FIG. 3, the tissue aperture creating assembly may have many forms. Some such forms are shown schematically in FIGS. 4A–4E. In FIG. 4A, an outwardly, facing blade 50 is disposed at the junction of the bifurcated portions. With this configuration, mere advancement of the apparatus 10$_a$" will effect cutting once the distal ends 16 and 26 are within the respective vessels BV1 and BV2. FIG. 4B shows an apparatus 10$_b$" having an elongated blade 52 on element 12 and an opposing anvil 54 on element 24. Similarly, FIG. 4C shows an apparatus 10$_c$" having a hole punch 56 on element 12 and an anvil 58 on element 22, together with a blade 50 at the junction of the bifurcated portions. This configuration is useful to cut an initial hole at the point CP and then a second hole separated therefrom by the distance of the hole punch 56 from the blade 50. FIG. 4D shows an apparatus 11$_d$" having an rf coil 60 on element 12, and a grounded element 62 on element 22, where coil 60 and ground element 62 are electrically coupled by wires 64 and 66 to an external rf generator. FIG. 4E shows a laser cutter 68 on element 12 which may be selectively actuated via wires 70, 72, to ablate tissue adjacent thereto.

All of the above catheter-configurations have an advantage over the rigid scissors-like configuration of FIGS. 1A and 1B. That advantage is that the veinotomy can be relatively remote from the initial cutpoint, (since the catheter can be of any desire length). In contrast, the scissors-like configurations of FIGS. 1A and 1B require externally applied forces on the handles to effect the cutting, where those forces must be applied relatively close to the initial cutpoint. In other forms, however, the scissors-like elements 12 and 22 may be remotely actuated by a conventional mechanical (or electrically driven) linkage.

The embodiment of FIG. 4A is particularly easy to use since mere advancement of the apparatus 10" effects cutting (via blade 50). The configurations of FIGS. 4B–4E require remote driving of the distal ends 16 and 26 toward each other, although this can be effected by using sheathed wires, as in the sidewall piercing device described above, or other conventional selectively actuatable closing assemblies.

Figure 5A:
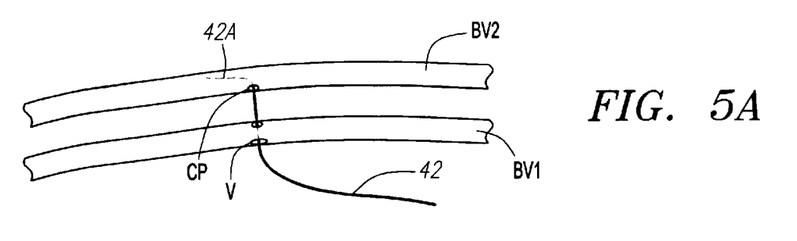
FIGS. 5A and 5B show deployments of a guidewire of the kit of the invention.
Figure 5B:
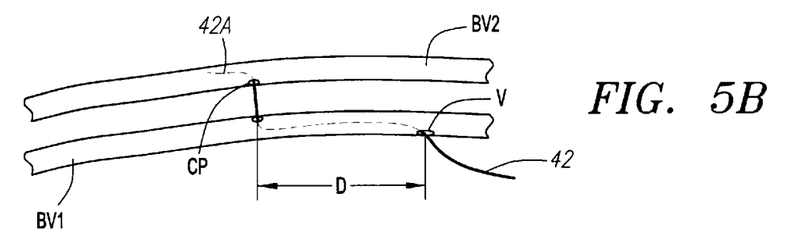
Figure 6:
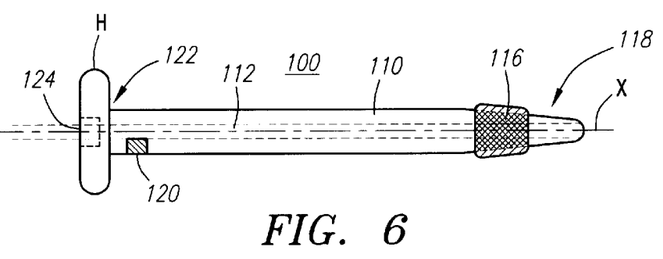
FIG. 6 is a schematic represenation of an over-the-wire aperture creating apparatus with a single elongate member, including a aperture creating element, an orientation marker and a hemostasis apparatus.

The embodiments of FIGS. 3–4E may be used with a guidewire 42 introduced at an access point V at or near or opposite to the initial cutpoint CP (as shown in FIG. 5A) or with a guidewire 42 introduced at a distance D from that initial cutpoint CP (as shown in FIG. 5B).

Figure 7:
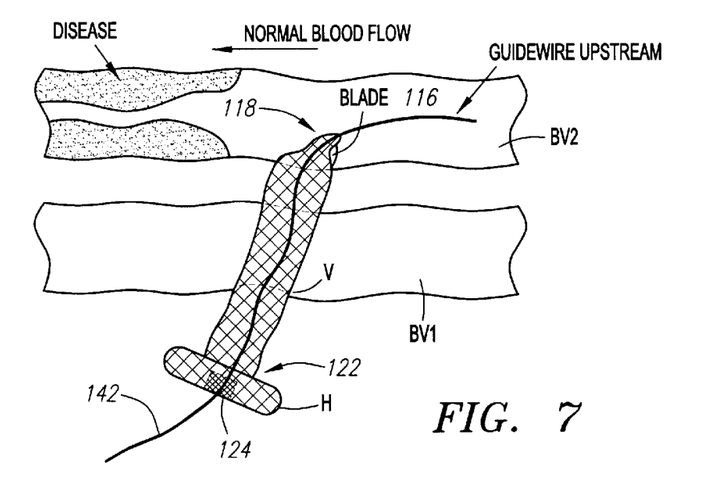
FIG. 7 illustrates a method of using a single elongate member device between blood vessels

Additional aperture creating apparatus forms of the invention adapted for following a single guidewire (in the configurations of FIGS. 5A and 5B) are shown in FIGS. 6–13B. An exemplary aperture creating apparatus 100 is shown generally in FIG. 6. That apparatus 100 includes an elongated element 110 having a central lumen 112 (for passage over a guidewire 42). The element 110 may be rigid or flexible, and includes a tissue cutting, tissue removing, tissue ablating or tissue enlarging element 116 at or near its distal tip 118. An optional angular orientation (about an axis of lumen 112) indicator 120 is shown near the proximal end 122 of element 110. A hemostasis valve 124 may optionally be positioned (e.g., near proximal end 122) on element 110 to block exit blood flow through lumen 112 while allowing passage of the guidewire, if desired. FIG. 7 shows the aperture creating apparatus 100 in use to establish a flowpath from a blood vessel upstream of a diseased segment to an adjacent vessel. In use, a suitable coupler or scaffold may be used to couple the apertures established by a blade B in aperture creating apparatus 100, so that a well-defined blood flowpath is established between the two vessels.

Figure 8:
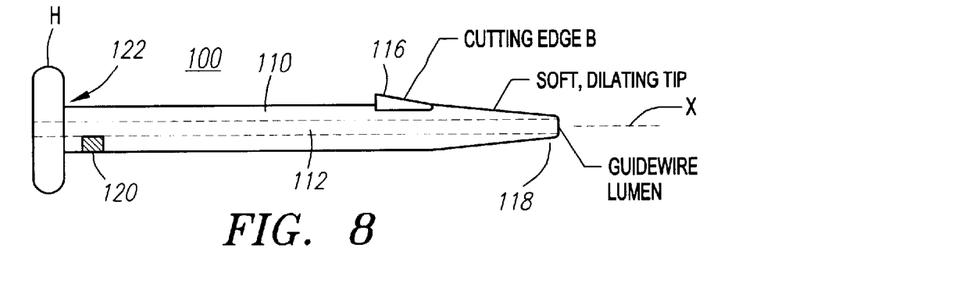
FIG. 8 is a schematic representation of an over-the-wire aperture creating apparatus with a single elongate member having an eccentric cutting edge.

FIG. 8 shows an exemplary form for the aperture creating apparatus 100 having a rigid element 110 with a blade B near distal tip 118 and a handle H at the proximal end 122. In this illustrated form, the distal end of element 110 is relatively soft or flexible. An orientation marker 120 is positioned near the proximal end 122.

Figure 9A:
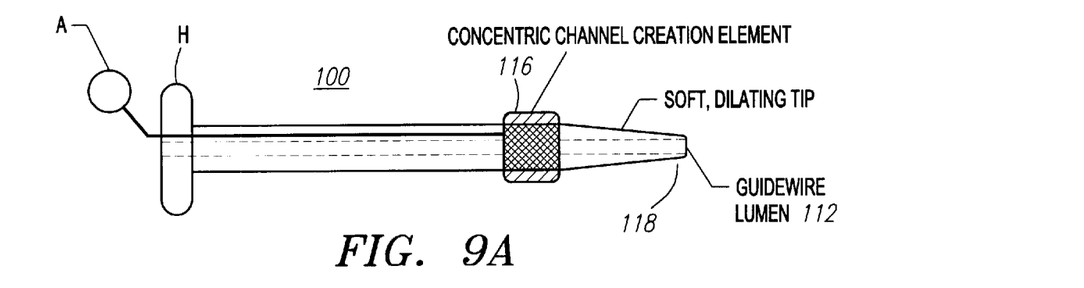
FIG. 9A is a schematic representation of an over-the-wire aperture creating apparatus with a single elongate member having a concentric channel creation element attached to an actuator.
Figure 9B:
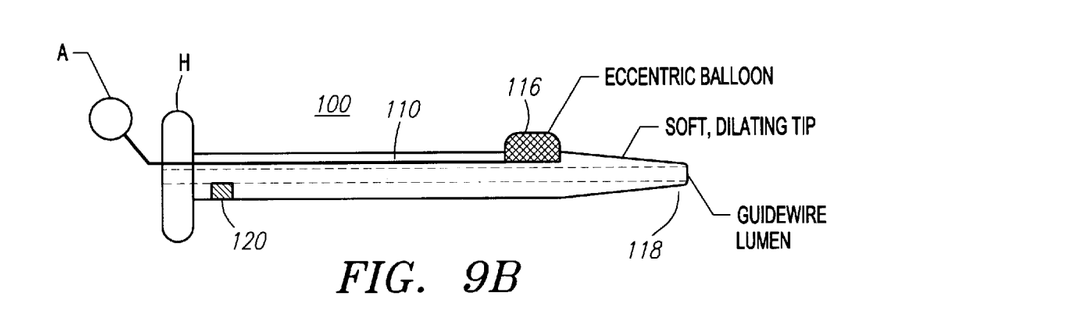
FIG. 9B is a schematic representation of an over-the-wire aperture creating apparatus with a single elongate member having an eccentric balloon attached to an actuator and an orientation marker.

FIGS. 9A and 9B show similar exemplary forms of aperture-creating apparatus 100 but where the tissue enlarging elements are in the form of remotely a deployable/inflatable concentric balloon 116 (FIG. 9A) and an eccentric balloon 716 (FIG. 9B). In the latter form, the orientation marker 120 is preferably employed so that in use the handle H may be used to rotate the element 110 and the resultant motion of the eccentric balloon is known. In FIGS. 9A and 9B, an actuator A is shown for selectively inflating the balloons.

Figure 10:
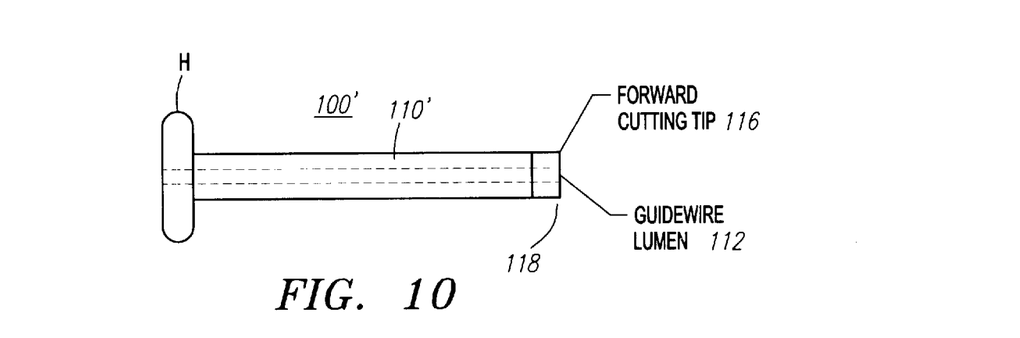
FIG. 10 is a schematic representation of an over-the-wire aperture creating apparatus with a single elongate member having a forward cutting distal tip.

FIG. 10 shows an aperture-creating apparatus 100' with an elongated element 110' with a central lumen 112 and having a handle H at its proximal end and a circular cutting edge 116 at its distal end 118. This apparatus 100' operates in a "push forward" mode where the user applies a force to the handle H to direct the cutting edge 116 against the vessel sidewalls.

Figure 11:
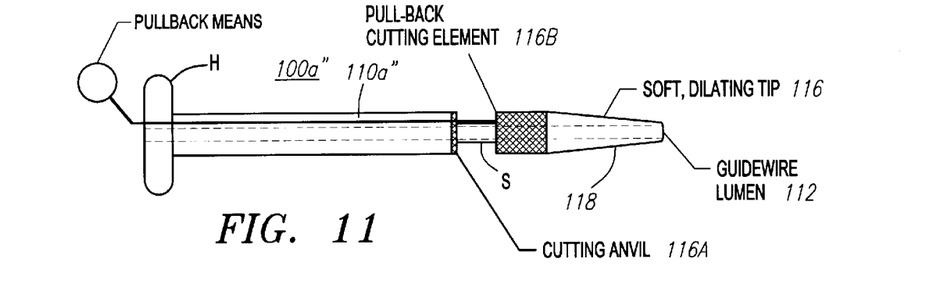
FIG. 11 is a schematic representation of an over-the-wire aperture creating apparatus with a single elongate member having a pull back cutting element and actuator with anvil.

FIG. 11 shows an aperture-creating apparatus 100$_a$" with a cylindrical shell 110$_a$" slidably disposed over a shaft S that has an inner guidewire lumen 112. The leading edge 116A forms an anvil against which a cutting edge 116B extending from the distal end of the shaft S may be driven in response to a pull-back force applied by a user.

Figure 12:
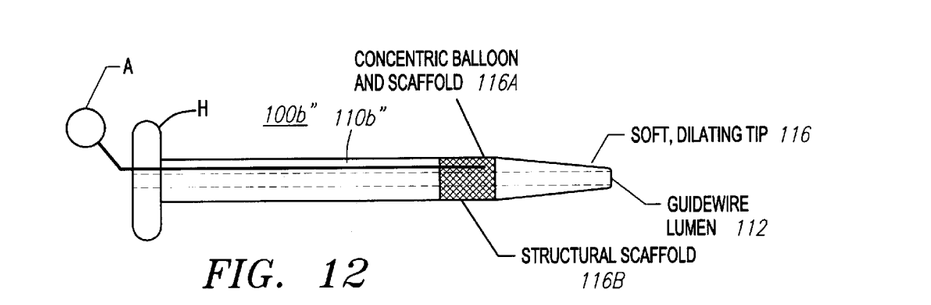
FIG. 12 is a schematic representation of an over-the-wire aperture creating apparatus with a single elongate member having a concentric balloon and actuator and alternatively a structural scaffold implant disposed thereon.

FIG. 12 shows another form of aperture-creating apparatus $100_b''$. That form includes a shaft $110_b''$ (including a guidewire lumen 112) with a concentric balloon 116A and optional scaffold 116B near its distal end 118. A remote actuator A is used to selectively inflate the balloon 116A. In operation, the balloon 116A will be inflated to create desired apertures. Optionally, the balloon 116A may include a scaffold member disposed thereon (e.g. a reinforced balloon) to aid in aperture creation. In some cases it may be desirable to permanently implant the scaffold member to further aid in creating a fluid path between the apertures.

Figure 13A:
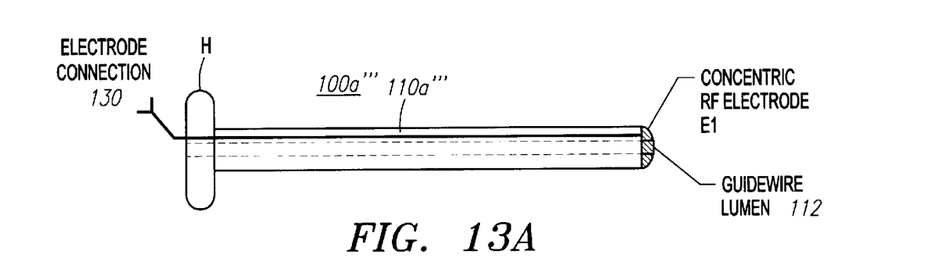
FIG. 13A is a schematic representation of an over-the-wire aperture creating apparatus with a single elongate member having a concentric RF electrode and proximal connection.
Figure 13B:
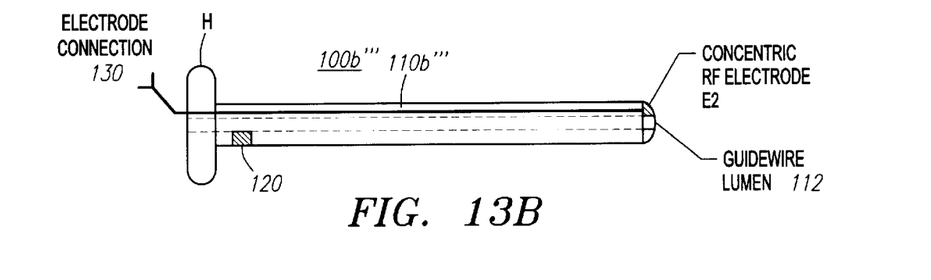
FIG. 13B is a schematic representation of an over-the-wire aperture creating apparatus with a single elongate member having an eccentric RF electrode and proximal connection including an orientation element.

FIGS. 13A and 13B show forms of aperture-creating apparatus 100''' wherein the aperture-creating element is either a concentric ablation electrode E1 (FIG. 137A) or an eccentric ablation electrode E2 (FIG. 13B). The electrodes E1, E2 may be selectively activated by way of electrode connections 130. An orientation marker 120 may be used with the eccentric electrode to allow the operator to direct the cutting energy.

The various forms of the aperture creating apparatus 100 in FIGS. 6–13B, where the element 110 is rigid, are preferably used with guidewire deployments of FIG. 5A. Forms of the aperture creating apparatus 100 in FIGS. 6–13B, where the element 110 is flexible, may be used with the guidewire deployments of both FIGS. 5A and 5B.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. An over-the-wire kit for simultaneously cutting a slit in adjacent portions of a first blood vessel and a second blood vessel during a surgical procedure comprising:
   A. a first guidewire for insertion into a lumen of the first vessel through adjacent portions of sidewalls of the first vessel and the second vessel into a lumen of the second vessel; and
   B. a wire-guided cutting assembly including:
      i. a first elongated element extending along a first axis between a proximal end and a distal end,
      ii. a second elongated element extending along a second axis between a proximal end and a distal end,
      iii. a coupler for coupling said first elongated element to said second elongated element whereby said first axis substantially intersects said second axis, and whereby said distal end of said first elongated element is movable with respect to said distal end of said second elongated element about an axis orthogonal to said first axis and said second axis, and
      iv. a tissue cutting assembly disposed between said first and second elongated elements,
      wherein at least one of said first and second elongated elements includes a passage-defining element permitting passage therethrough of said first guidewire,
      wherein at least one of said first and second elongated elements is flexible at least near said distal end, and
   wherein said tissue cutting assembly includes:
      a blade at a point of coupling of said first and second elongated elements, wherein said blade faces away from said point of coupling.

2. A kit according to claim 1 wherein both of said first and second elongated elements are flexible at least near said distal ends.

3. An over-the-wire kit for simultaneously cutting a slit in adjacent portions of a first blood vessel and a second blood vessel during a surgical procedure comprising:
   A. a first guidewire for insertion into a lumen of the first vessel through adjacent portions of sidewalls of the first vessel and the second vessel into a lumen of the second vessel; and
   B. a wire-guided cutting assembly including:
      i. a first elongated element extending along a first axis between a proximal end and a distal end,
      ii. a second elongated element extending along a second axis between a proximal end and a distal end,
      iii. a coupler for coupling said first elongated element to said second elongated element whereby said first axis substantially intersects said second axis, and whereby said distal end of said first elongated element is movable with respect to said distal end of said second elongated element about an axis orthogonal to said first axis and said second axis, and
      iv. a tissue cutting assembly disposed between said first and second elongated elements
   wherein at least one of said first and second elongated elements includes a passage-defining element permitting passage therethrough of said first guidewire, the kit farther comprising a second guidewire for insertion into a lumen of the first vessel, and wherein each of said first and second elongated elements includes a passage-defining element permitting passage therethrough of an associated one of said first and second guidewires.

4. A kit according to claim 3 wherein said first and second elongated elements are rigid and said coupling is a pivotal coupling about said orthogonal axis.

5. A kit according to claim 4, wherein said wire-guided cutting assembly is a scissors wherein each of said first and second elongated elements extends in a first direction from said intermediate point and has a handle cutting control element extending from said intermediate point in a direction at least in part opposite to the said direction,
   wherein said pivotal coupling is at said intermediate point on said first and second elongated elements to form a pair of opposed cutting elements.

6. A kit according to claim 5 wherein a bisector of an angle formed by said first and second axes of said opposing cutting elements is angularly offset with respect to a bisector of an angle formed by said first and second axes of said handle cutting control elements.

7. A kit according to claim 3 wherein at least one of said first and second elongated elements is flexible at least near said distal end.

8. A kit according to claim 7 wherein said tissue cutting assembly includes:
   a blade at a point of coupling of said first and second elongated elements, wherein said blade faces away from said point of coupling.

9. A kit according to claim 3 wherein said tissue cutting assembly includes:
   a blade at a point of coupling of said first and second elongated elements, wherein said blade faces away from said point of coupling.

10. A kit according to claim 3 wherein said tissue cutting assembly includes
a hole punch on one said first and second elongated elements, said hole punch facing the other of said first and second elongated elements, and an anvil on said elongated element not having said hole punch, said anvil being opposite said hole punch.

11. A wire guided cutting apparatus for simultaneously cutting a slit in adjacent portions of a first blood vessel and a second blood vessel during a surgical procedure comprising:
A. a first elongated element extending along a first axis between a proximal end and a distal end;
B. a second elongated element extending along a second axis between a proximal end and a distal end;
C. a coupler for coupling said first elongated element to said second elongated element whereby said first axis substantially intersects said second axis, and whereby said distal end of said first elongated element is movable with respect to said distal end of said second elongated element about an axis orthogonal to said first and second axes; and
D. a tissue cutting assembly disposed between said first and second elongated elements, said tissue cutting assembly including a hole punch on one said first and second elongated elements, said hole punch facing the other of said first and second elongated elements, and an anvil on said elongated element not having said hole punch, said anvil being opposite said hole punch;
wherein each of said first and second elongated elements includes a passage-defining element permitting passage therethrough of an associated one of said first guidewire and a second guidewire.

12. A method for creating a hole in adjacent portions of a first blood vessel and a second blood vessel during a surgical procedure, comprising the steps of:
A. introducing a lead end of a first guidewire into a lumen of the first vessel and advancing said lead end through adjacent portions of sidewalls of the first vessel and the second vessel and into a lumen of the second vessel;
B. providing a wire guided cutting apparatus including:
i. a first elongated element extending along a first axis between a proximal end and a distal end,
ii. a second elongated element extending along a second axis between a proximal end and a distal end,
iii. a coupler for coupling said first element to said second element whereby said first axis substantially intersects said second axis, and whereby said distal end of said first element is movable with respect to said distal end of said second element about an axis orthogonal to said first axis and said second axis at said intersection of said first axis and said second axis, and
iv. a tissue cutting assembly disposed between said first and second elongated elements,
wherein a least one of said first and second elongated elements includes a passage-defining element permitting passage therethrough of said first guidewire; and
C. positioning said wire guided cutting apparatus over said first guidewire such that said passage-defining element passes over said first guidewire,
D. advancing said first and second elongated elements into said lumen of said first vessel and along said lumen whereby said first elongated element follows said first guidewire along said lumen of said first vessel and through said sidewalls of said first and second vessels and into said lumen of said second vessel which said second elongated element remains in said lumen of said first vessel, and
E. causing said tissue cutting assembly to cut tissue between said first and second elongated elements.

13. A method according to claim 12 further comprising the step of introducing a lead end of a second guidewire into said lumen of said first vessel and advancing said lead end in said lumen beyond said initial cutpoint,
wherein said providing step comprises providing said wire guided cutting apparatus wherein each of said first and second elongated elements has a passage-defining element permitting passage therethrough of an associated one of said first and second guidewires; and
wherein said positioning step comprises positioning said wire guided cutting apparatus over said first guidewire and said second guidewire such that said passage-defining element of one of said first and second elongated elements passes over one of said first and second guidewires, and said passage-defining element of the other of said first and second elongated elements passes over the other of said first and second guidewires.

14. An over-the-wire kit for simultaneously cutting a slit in adjacent portions of a first blood vessel and a second blood vessel during a surgical procedure, comprising:
a first guidewire for insertion into a lumen of the first vessel and through a sidewall of the first vessel into a lumen of the second vessel; and
a wire-guided cutting assembly including:
a first elongated element extending along a first axis between a proximal end and a distal end;
a second elongated element extending along a second axis between a proximal end and a distal end, the second elongated element being pivotably coupled to the first elongated element; and
a tissue cutting assembly disposed between the first and second elongated elements;
wherein each of the first and second elongated elements includes a tubular element permitting passage therethrough of the first guidewire and a second guidewire, respectively.

15. A kit according to claim 14, wherein the first and second elongated elements are rigid.

16. A kit according to claim 14, wherein the wire-guided cutting assembly is a pair of opposing cutting elements extending in a fist direction from a pivotal coupling point, arid a pair of handle cutting control elements extending from the pivotal coupling point in a direction at least in part opposite to the first direction.

17. A kit according to claim 14, wherein at least one of the first and second elongated elements is flexible at least near said distal end.

18. A kit according to claim 17, wherein the tissue cutting assembly includes a blade at the pivotal coupling point of the first and second elongated elements, the blade facing away from a coupling point where the second elongated element is pivotably coupled to the first elongated element.

19. A kit according to claim 17, wherein both of the first and second elongated elements are flexible at least near their distal ends.

20. A kit according to claim 14, wherein the tissue cutting assembly comprises a cooperating blade and anvil on the first and second elongated elements.

21. An over-the-wire kit for simultaneously cutting a slit in adjacent portions of a first blood vessel and a second blood vessel during a surgical procedure, comprising:

a first guidewire for insertion into a lumen of the first vessel and through a sidewall of the first vessel into a lumen of the second vessel; and a wire-guided cutting assembly including:
- a first elongated element extending along a first axis between a proximal end and a distal end;
- a second elongated element extending along a second axis between a proximal end and a distal end, the second elongated element being pivotably coupled to the first elongated element;
- a tissue cutting assembly disposed between the first and second elongated elements; and a second guidewire for insertion into a lumen of the first vessel, and wherein each of the first and second elongated elements comprises a tubular element permitting passage therethrough of one of the first and second guidewires.

22. A wire-guided cutting apparatus for simultaneously cutting a slit in adjacent portions of a first blood vessel and a second blood vessel during a surgical procedure comprising:
- a first elongated element comprising a proximal end, a distal end insertable into a first blood vessel, and a first axis therebetween, the first elongated element comprising a first tubular element comprising proximal and distal ends on the distal end of the first elongated element and comprising coaxial proximal and distal openings in the proximal and distal ends of the first tubular element for permitting passage therethrough of a first guidewire;
- a second elongated element comprising a proximal end, a distal end insertable into a second blood vessel, and a second axis therebetween, the second elongated element being pivotably coupled to the first elongated element, the second elongated element comprising a second tubular element comprising proximal and distal ends on the distal end of the second elongated element and comprising coaxial proximal and distal openings in the proximal and distal ends of the second tubular element for permitting passage therethrough of a second guidewire; and
- a tissue cutting assembly disposed between the first and second elongated elements.

23. A wire-guided cutting apparatus according to claim 22, wherein each of the passage-defining elements comprises a pair of ring-like guides.

24. A wire-guided cutting apparatus according to claim 22, wherein the passage-defining elements comprise channels extending through the first and second elongate elements, respectively.

25. A wire-guided cutting apparatus according to claim 22, wherein the first and second elongated elements are substantially rigid.

26. A wire-guided cutting apparatus according to claim 25, wherein the wire-guided cutting apparatus comprises opposing cutting elements extending in a first direction from an intermediate point, and a handle cutting control element extending from the intermediate point in a direction opposite to the first direction, the second elongated element being pivotably coupled to the first elongated element at the intermediate point.

27. A wire-guided cutting apparatus according to claim 26, wherein a bisector of an angle formed by the first and second axes of the opposed cutting elements is angularly offset with respect to a bisector of an angle formed by the first and second axes of the handle cutting control element.

28. A wire-guided cutting apparatus according to claim 22, wherein at least one of the first and second elongated elements is flexible at least near their distal ends.

29. A wire-guided cutting apparatus according to claim 22, wherein both of the first and second elongated elements are flexible at least near their distal ends.

30. A wire-guided cutting apparatus according to claim 22, wherein the tissue cutting assembly includes a blade at a point of coupling of the first and second elongated elements, the blade facing away from the point of coupling.

31. A wire-guided cutting apparatus according to claim 22, wherein the tissue cutting assembly comprises a cooperating blade and anvil on the first and second elongated elements.

32. An over-the-wire kit for simultaneously cutting a slit in adjacent portions of a first blood vessel ad a second blood vessel during a surgical procedure, comprising:
- a first guidewire for insertion into a lumen of the first vessel and through a sidewall of the first vessel into a lumen of the second vessel; and
- a wire-guided cutting assembly including:
  - a first elongated element extending along a first axis between a proximal end and a distal end, the first elongated element comprising a passage-defining element permitting passage therethrough of the firs guidewire;
  - a second elongated element extending along a second axis between a proximal end and a distal end, the second elongated element being pivotably coupled to the firs elongated element, the second elongated element comprising a passage-defining element permitting passage therethrough of a second guidewire; and
  - a tissue cutting assembly disposed between the first and second elongated elements; and
- a second guidewire for insertion into a lumen of the first vessel, the second guidewire being insertable through the passage-defining element of the second elongated element.

* * * * *

UNITED STATES PATENT AND TRADEMARK OFFICE
CERTIFICATE OF CORRECTION

PATENT NO. : 6,685,716 B1 Page 1 of 1
APPLICATION NO. : 09/478109
DATED : February 3, 2004
INVENTOR(S) : J. Christopher Flaherty et al.

It is certified that error appears in the above-identified patent and that said Letters Patent is hereby corrected as shown below:

Column 12, line 48, "arid a pair" should be changed to -- and a pair --

Signed and Sealed this

Ninth Day of January, 2007

JON W. DUDAS
*Director of the United States Patent and Trademark Office*